United States Patent
Miyai et al.

(10) Patent No.: US 9,255,917 B2
(45) Date of Patent: Feb. 9, 2016

(54) ANALYZER CALIBRATING SYSTEM AND EXHAUST GAS ANALYZING SYSTEM

(71) Applicant: HORIBA, Ltd., Kyoto (JP)

(72) Inventors: Masaru Miyai, Kyoto (JP); Hiroshi Nakamura, Kyoto (JP); Masahiro Nishikawa, Kyoto (JP)

(73) Assignee: HORIBA, Ltd., Kyoto (JP)

( * ) Notice: Subject to any disclaimer, the term of this patent is extended or adjusted under 35 U.S.C. 154(b) by 401 days.

(21) Appl. No.: 13/900,175

(22) Filed: May 22, 2013

(65) Prior Publication Data

US 2013/0312482 A1    Nov. 28, 2013

(30) Foreign Application Priority Data

May 22, 2012    (JP) ................... 2012-117043

(51) Int. Cl.
   *G01N 33/00*         (2006.01)
(52) U.S. Cl.
   CPC .................. *G01N 33/0006* (2013.01)
(58) Field of Classification Search
   CPC ........................ G01N 33/0006; G01N 21/3504
   USPC .......................................................... 73/1.06
   See application file for complete search history.

(56) References Cited

U.S. PATENT DOCUMENTS

| | | | | |
|---|---|---|---|---|
| 3,630,437 A | * | 12/1971 | Swanson | G05D 23/1905 236/51 |
| 4,489,590 A | * | 12/1984 | Hadden | G01N 33/0006 73/1.04 |
| 4,555,930 A | * | 12/1985 | Leach | G01N 27/122 73/1.07 |
| 5,239,492 A | * | 8/1993 | Hartwig | G01N 33/0006 702/27 |
| 5,509,292 A | | 4/1996 | d'Appollonia et al. | |
| 5,627,328 A | * | 5/1997 | Sheridan | G01N 1/2258 73/863.83 |
| 5,804,695 A | | 9/1998 | Dageforde | |
| 5,894,083 A | | 4/1999 | Hiraoka et al. | |
| 7,530,255 B2 | * | 5/2009 | Frank | G01N 33/0006 73/1.03 |
| 2003/0000281 A1 | * | 1/2003 | Ketler | G01N 33/0006 73/1.06 |
| 2004/0055359 A1 | | 3/2004 | Ketler et al. | |
| 2012/0260715 A1 | | 10/2012 | Miyai et al. | |
| 2014/0349408 A1 | * | 11/2014 | Skourlis | G01N 33/0006 436/149 |

FOREIGN PATENT DOCUMENTS

| | | |
|---|---|---|
| DE | 3819100 A1 | 12/1989 |
| DE | 19926139 A1 | 12/2000 |
| EP | 0345563 A2 | 12/1989 |
| JP | 02-115741 | 4/1990 |

(Continued)

OTHER PUBLICATIONS

Office Action dated Sep. 21, 2015 issued for Chinese Patent Application No. 201310176521.8, 10 pgs.

*Primary Examiner* — Freddie Kirkland, III
(74) *Attorney, Agent, or Firm* — Brooks Kushman P.C.

(57) ABSTRACT

An analyzer calibrating system intended to reduce calibration time and a consumption amount of calibration gas in the case of concurrently calibrating a plurality of analyzers and includes: a calibration gas line for concurrently supplying the same calibration gas to a plurality of analyzers; and a control unit adapted to determine whether or not an output value of each of the plurality of analyzers supplied with the same calibration gas is stable. The control unit calibrates the analyzer having the output value determined to be stable and stops the supply of the calibration gas to the analyzer having completed with the calibration.

3 Claims, 4 Drawing Sheets

(56) References Cited

FOREIGN PATENT DOCUMENTS

| | | |
|---|---|---|
| JP | 03-009255 | 1/1991 |
| JP | 06-331512 | 12/1994 |
| JP | 07-198693 | 8/1995 |
| JP | 08233738 | 9/1996 |
| JP | 10-132710 | 5/1998 |
| JP | 2000-146984 | 5/2000 |
| JP | 2001-221720 | 8/2001 |
| JP | 2006-003115 | 1/2006 |

* cited by examiner

ANALYZER CALIBRATING SYSTEM AND EXHAUST GAS ANALYZING SYSTEM

CROSS-REFERENCE TO RELATED APPLICATION

This application claims priority to JP Application No. 2012-117043, filed on May 22, 2012, the disclosure of which is incorporated in its entirety by reference herein.

TECHNICAL FIELD

The present invention relates to an analyzer calibrating system capable of concurrently calibrating a plurality of analyzers and an exhaust gas analyzing system using the analyzer calibrating system.

BACKGROUND ART

An exhaust gas analyzer for analyzing exhaust gas exhausted from an engine of a vehicle or the like is used in arrangement in each of a plurality of test chambers. In each of the test chambers, an engine of such as a vehicle serving as a specimen is installed.

Then, in the case of calibrating these exhaust gas analyzers, it is necessary to supply calibration gas for zero calibration or span calibration to flow through the exhaust gas analyzers. In this arrangement, since a calibration gas cylinder storing the calibration gas is in a state of high pressure, the calibration gas cylinder is usually provided in a gas cylinder chamber separated from the test chambers. In addition, since the calibration gas is supplied to a plurality of exhaust gas analyzers from the calibration gas cylinder in common, the number of calibration gas cylinders is reduced.

However, in the conventional case where the calibration gas is concurrently supplied from one calibration gas cylinder to a plurality of exhaust gas analyzers to be calibrated, calibration time is uniformly set for all of the exhaust gas analyzers. In addition, during this calibration time, it is configured to render the calibration gas to flow into all of the exhaust gas analyzers.

In this arrangement, a time until an output value of each exhaust gas analyzer becomes stable is different depending on a length of a calibration gas pipe between the calibration gas cylinder and the exhaust gas analyzer and a status of a contact gas surface of the calibration gas pipe or piping conditions such as a material of the calibration gas pipe and a situation of such as an installation environment of each of the exhaust gas analyzers. For example, in an exhaust gas analyzer having a lengthy pipe from the calibration gas cylinder, it takes a long time for the calibration gas to reach the exhaust gas analyzer so that the time to stabilize the output value of the exhaust gas analyzer is accordingly increased. Moreover, as described above, in the case where the calibration time is uniformly set for all of the exhaust gas analyzers, it is necessary also for an exhaust gas analyzer having completed with the calibration with the output value already stabilized to wait for a lapse of the calibration time, and there arises a problem that a start of a measurement of the exhaust gas using the exhaust gas analyzer is delayed. Furthermore, in spite that the calibration can be early finished for the exhaust gas analyzer having completed with the calibration with the output value already stabilized, the calibration gas is unnecessarily continued to flow into the exhaust gas analyzer, and there arises also a problem that the calibration gas is consumed in waste.

SUMMARY OF INVENTION

Technical Problem

Therefore, the present invention has been made in order to solve the problems at a stroke and its essential object is to reduce the calibration time and consumption amount of calibration gas in the case of concurrently calibrating a plurality of analyzers.

Solution to Problem

That is, an analyzer calibrating system according to the present invention is characterized by including: a calibration gas line for concurrently supplying the same calibration gas to a plurality of analyzers; and a control unit adapted to determine whether or not an output value of each of the plurality of analyzers supplied with the same calibration gas is stable, whereby the control unit calibrates the analyzer having the output value determined to be stable and stops the supply of the calibration gas to the analyzer having completed with the calibration. It is noted here that the phrase "concurrently supplying the same calibration gas to a plurality of analyzers" means not only an idea of starting the supply of the calibration gas to a plurality of analyzers at the same time but also includes an idea that there is a time period of supplying the calibration gas to a plurality of analyzers at the same time during a calibration process even in the case where the starting times of supplying the calibration gas to a plurality of analyzers are different.

With this configuration, the calibration gas for a plurality of analyzers can be concurrently supplied via the calibration gas line so that the plurality of analyzers can be concurrently calibrated. In addition, since the control unit determines whether or not an output value of each of the plurality of analyzers is stable and calibrates the analyzer having the output value determined to be stable so that the supply of the calibration gas to the analyzer having completed with the calibration is stopped, the calibration time can be optimized for every analyzer so that the calibration time in total can be reduced. Further, since the calibration gas is not supplied in waste to the analyzer having completed with the calibration, the consumption amount of the calibration gas can be reduced.

As a simple and easy configuration for individually switching the supply and stop of the calibration gas to a plurality of analyzers, it may be considered that the calibration gas line includes a plurality of branch lines respectively provided in a one-to-one correspondence with the plurality of analyzers and a plurality of on/off valves respectively provided on the plurality of branch lines. In this configuration, it is preferable that the control unit controls the on/off valve provided on each of the branch lines to thereby stop the supply of the calibration gas to the analyzer having completed with the calibration.

In order to optimize the calibration time of the plurality of analyzers in any of the zero calibration and the span calibration, it is preferable that the calibration gas line includes a zero gas line for supplying zero gas for zero calibration to the plurality of analyzers and a span gas line for supplying span gas for span calibration to the plurality of analyzers and the control unit is configured to carry out the zero calibration using the zero gas and the span calibration using the span gas in this order.

Advantageous Effects of Invention

According to the present invention configured as described above, it becomes possible to reduce the calibration time together with the consumption amount of the calibration gas in the case of concurrently calibrating a plurality of analyzers.

DESCRIPTION OF EMBODIMENTS

The following describes one embodiment of an exhaust gas analyzing system according to the present invention with reference to the accompanying drawings.

Figure 1:
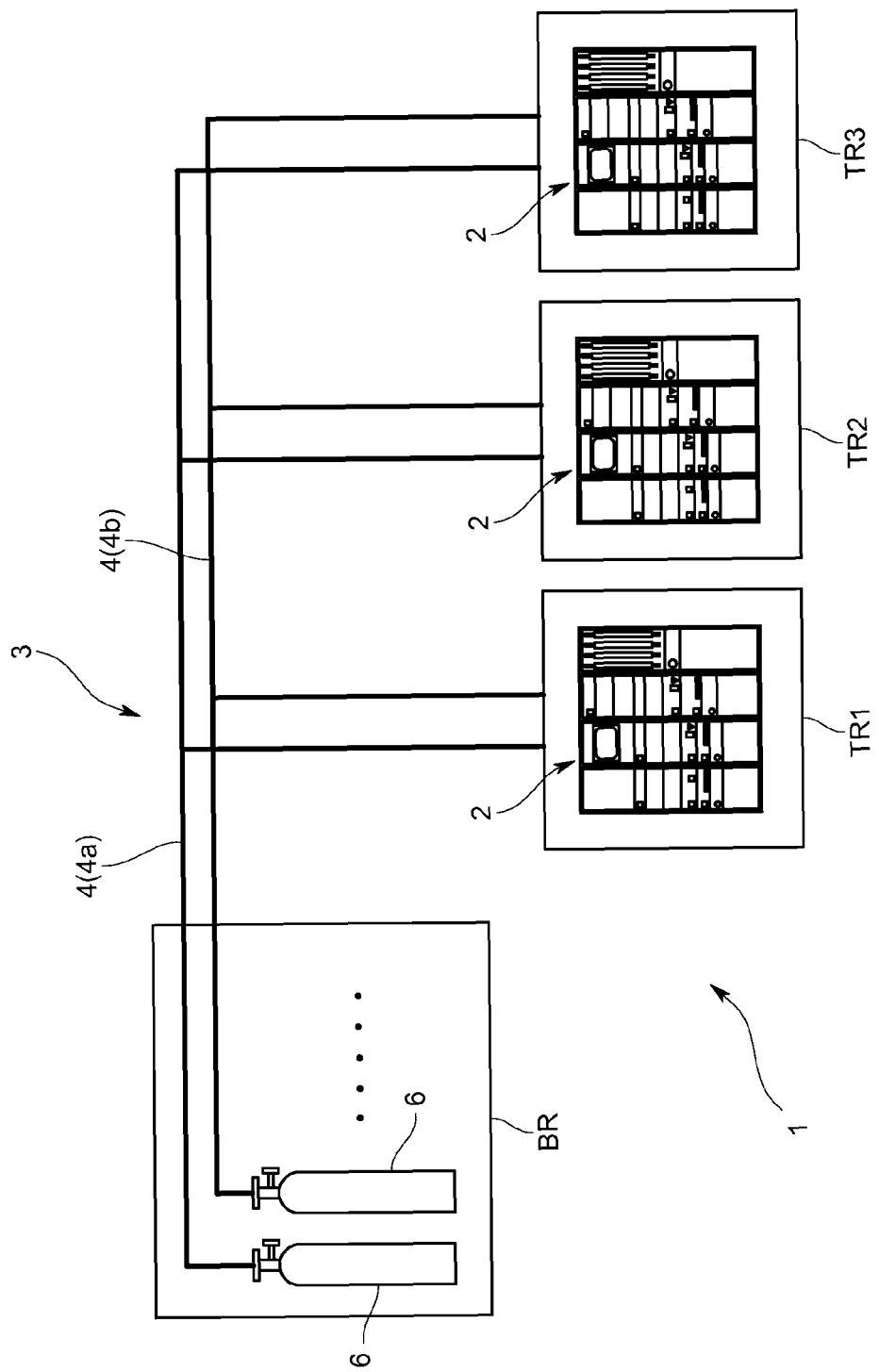
FIG. 1 is a schematic diagram showing a configuration of an exhaust gas analyzing system of the present embodiment.

As shown in FIG. 1, the exhaust gas analyzing system 1 of the present embodiment includes: a plurality of exhaust gas analyzing apparatuses 2 respectively provided in a plurality of test chambers TR1 to TR3 in FIG. 1 in each of which an engine of a vehicle or the like is installed to analyze the exhaust gas exhausted from the engine; and an analyzer calibrating system 3 for calibrating the plurality of exhaust gas analyzing apparatuses 2. In the arrangement of the plurality of exhaust gas analyzing apparatuses 2, lengths of calibration gas pipes from a calibration gas cylinder 6 as to be described later, statuses of contact gas surfaces of the calibration gas pipes or piping conditions such as materials of the calibration gas pipes and installation environment of each of the exhaust gas analyzers are different from each other.

In specific, the exhaust gas analyzing apparatus 2 is equipped with a plurality of analyzers having, for example, different measurement principles so as to be able to separately measure each component such as HC, NOX, CO, CO2 and the like contained in the exhaust gas. In addition, the analyzer configurations of the exhaust gas analyzing apparatus 2 arranged in each of the test chambers TR1 to TR3 may be identical to each other or may include an analyzer which is pertly different. It is noted that the plurality of exhaust gas analyzing apparatuses 2 send and receive various kinds of data such as analysis data, schedule data and the like to and from a central management device (not shown) located in a measurement chamber partitioned from the test chambers TR1 to TR3 via such as a LAN.

Figure 2:
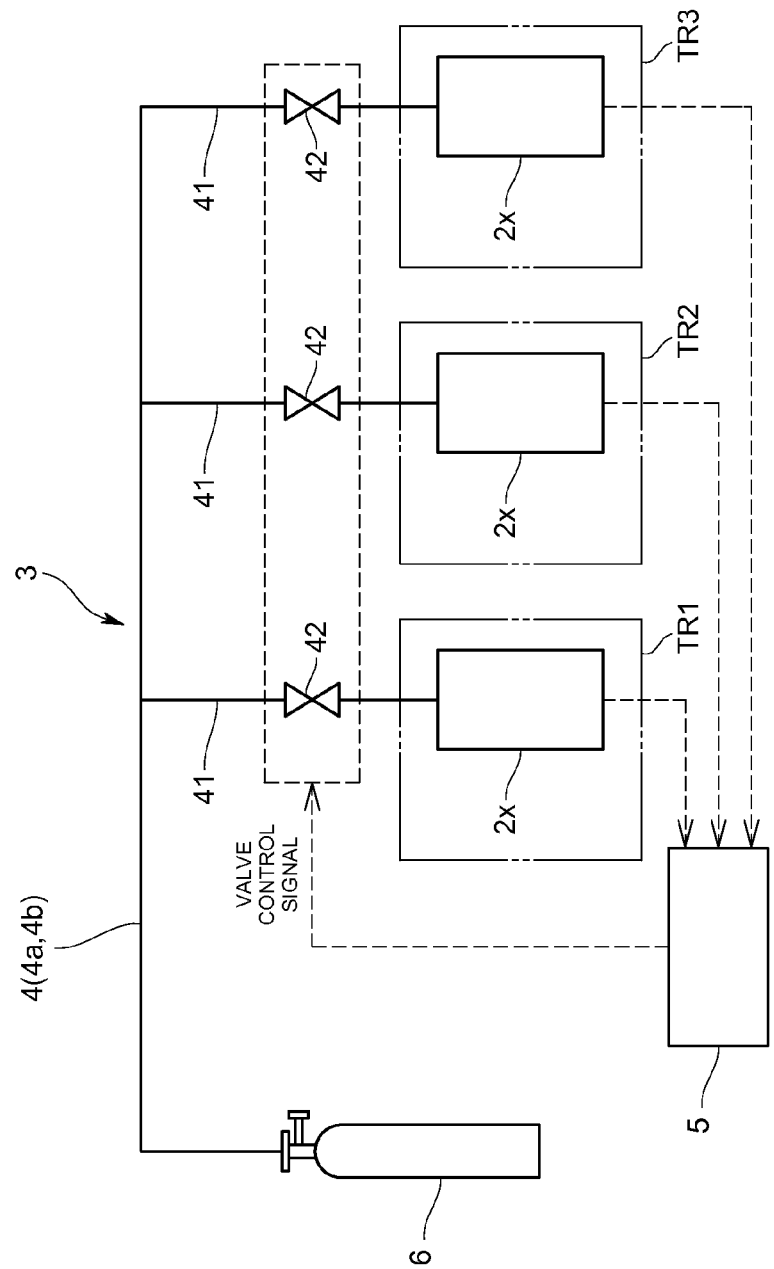
FIG. 2 is a schematic diagram showing a single calibration gas line of the same embodiment.

As shown in FIGS. 1 and 2, the analyzer calibrating system 3 includes: a plurality of calibration gas lines 4 provided for respective different kinds of calibration gas for concurrently supplying the calibration gas to the plurality of exhaust gas analyzing apparatuses 2; and a control unit 5 for controlling the calibration gas lines 4 and carrying out calibration processes of the plurality of exhaust gas analyzing apparatuses 2.

In this arrangement, as the different kinds of calibration gas, there are used zero gas for zero-calibrating the analyzer 2x, span gas for span-calibrating the analyzer 2x and the like and these different kinds of calibration gas are respectively supplied to different analyzers 2x of each exhaust gas analyzing apparatus 2. It is noted here that the reference numeral 2x shown in FIG. 2 denotes the identical analyzers that are calibrated using the same calibration gas in common to the plurality of exhaust gas analyzing apparatuses 2.

The calibration gas line 4 of the present embodiment includes: a zero gas line 4a for supplying zero gas for zero-calibrating the same analyzers 2x in the plurality of exhaust gas analyzing apparatuses 2 to the corresponding analyzers 2x; and a span gas line 4b for supplying span gas for span-calibrating the same analyzers 2x in the plurality of exhaust gas analyzing apparatuses 2 to the corresponding analyzers 2x. It is noted here that these zero gas line 4a and span gas line 4b are prepared for every kind of the analyzers 2x.

Especially as shown in FIG. 2, each calibration gas line 4 (4a, 4b) has its one end connected to a calibration gas cylinder 6 for storing the calibration gas, and includes a plurality of branch lines 41 branched in a one-by-one correspondence with the plurality of analyzers 2x in a downstream side thereof and further includes a plurality of on/off valves 42 such as solenoid valves respectively provided on the plurality of branch lines 41. The plurality of branch lines 41 are respectively provided for the same analyzers 2x constituting the exhaust gas analyzing apparatuses 2 respectively provided in the test chambers TR1 to TR3. The calibration gas cylinder 6 connected with each calibration gas line 4 is arranged in a cylinder chamber BR partitioned from the test chambers TR1 to TR3 and the measurement chamber.

The control unit 5 is adapted to determine whether or not an output value of each of the plurality of analyzers 2x is stable and calibrate the analyzer 2x having the output value determined to be stable, and then stops the supply of the calibration gas to the analyzer 2x having completed with the calibration thereof by controlling the calibration gas line 4.

Further, the control unit 5 continuously carries out the zero calibration using the zero gas and the span calibration using the span gas in this order. Then, in any of the zero calibration and the span calibration, the control unit 5 individually determines whether or not the output value of every analyzer 2x and controls each of the on/off valves 42 of the respective branch lines 41 to thereby switch the supply and stop of the calibration gas every analyzer 2x. It is noted that, as an equipment configuration of the control unit 5, it may be configured to function by a computer including, for example, a CPU, memory, I/O interface, AD converter, display and the like, or may be configured to function by a plurality of computers physically separated. Also, the functions of the control unit 5 may be provided in the central management device.

Figure 3:
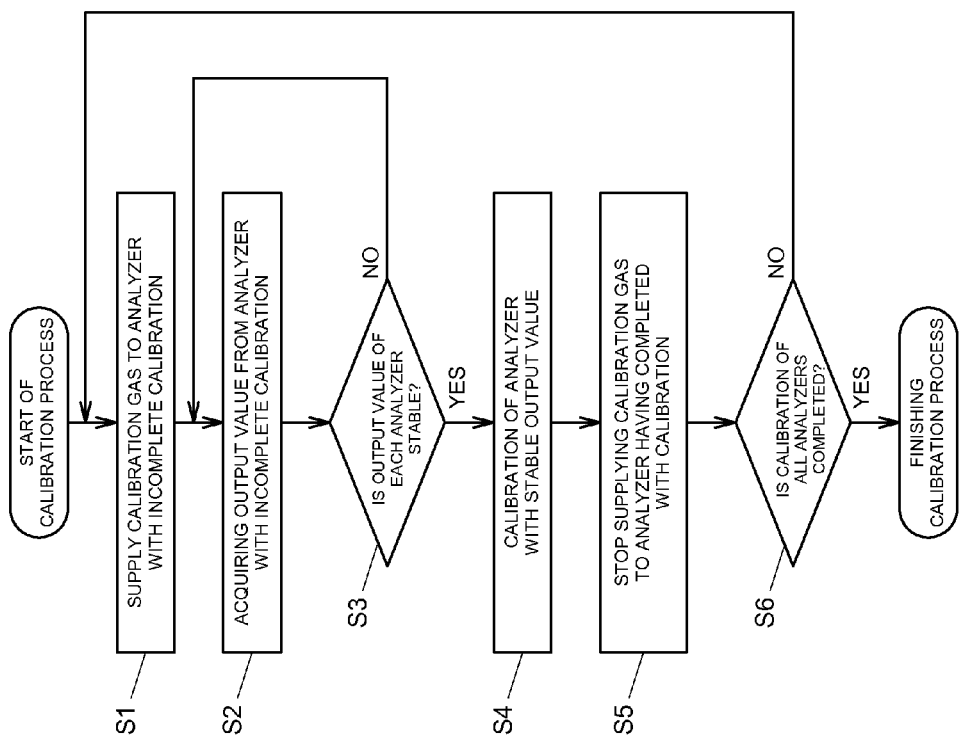
FIG. 3 is a flowchart of a calibration process of the same embodiment.

Specifically, the control unit 5 is adapted to control each of the on/off valves 42 on the branch lines 41 to thereby introduce the calibration gas to the plurality of analyzers 2x. That is, as shown in FIG. 3, at the time of starting the calibration process of the plurality of analyzers 2x, the control unit 5 opens an output port of the calibration gas cylinder 6 to be supplied to the analyzer 2x to be calibrated and opens the on/off valve 42 provided on the branch line 41 of the calibration gas line 4. Thus, the supply of the calibration gas to the plurality of analyzers 2x is started at the same timing (Step S1).

Figure 4:
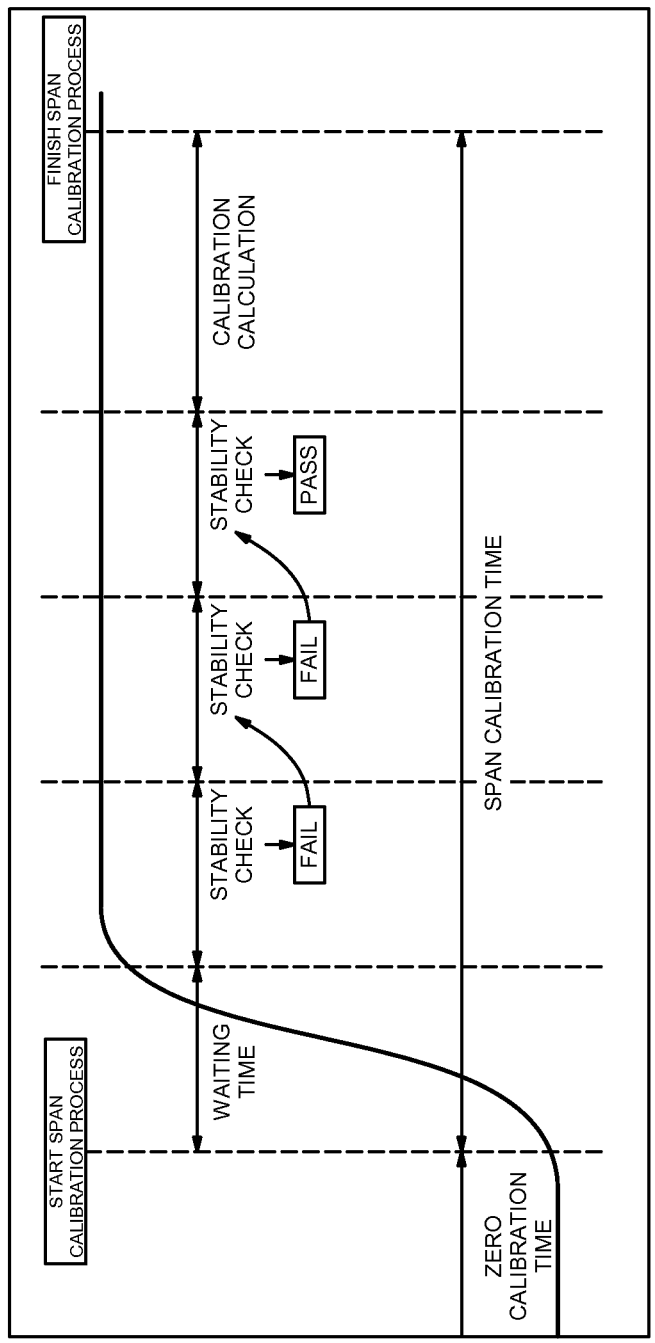
FIG. 4 is a schematic diagram showing a calibration method of the same embodiment.

Next, the control unit 5 acquires output value data obtained by the plurality of analyzers 2x supplied with the calibration gas (Step S2) and determines whether or not the output value of each of the plurality of analyzers 2x is stable (Step S3). Specifically, as shown in FIG. 4, after starting the supply of the span gas as the calibration gas, it is determined at predetermined time intervals whether or not the output value of each analyzer 2x is stable. The determination of stability of the output value is performed based on whether or not a predetermined condition is satisfied. In the present embodiment, the determination is performed based on whether or not a time-based variation width of the output value is within a predetermined range such as, for example, within 0.1% with respect to, for example, a full scale of the analyzer 2x. Then, according to the above determination, in the case where it is determined that the output value is stable, the output value and a known component concentration of the span gas are compared using the output valued thereafter to thereby perform the calibration of the analyzer 2x (Step S4). Meanwhile, in the case where the output value is not stable, the calibration gas is kept flowing until the output value is stable. The above is a calibration process of each analyzer. In FIG. 4, although the span calibration after the zero calibration is shown, the zero calibration performed before the span calibration is similarly performed. It is noted that, in FIG. 4, although a waiting time is set in consideration of replacement of the gas from the zero gas to the span gas at the time of starting the span calibration process after completion of the zero calibration, the stability of the output value may be determined at a predetermined time interval using a span calibration process starting point as a starting point without setting a waiting time.

After the above calibration is completed, the control unit 5 closes the on/off valve 42 on the branch line 41 connected to the analyzer 2x upon completion of the calibration thereof, thereby stopping the supply of the calibration gas to the analyzer 2x (Step S5). Regarding the analyzer 2x upon completion of the calibration thereof, the next exhaust gas measurement can be performed. Meanwhile, the control unit 5 continuously keeps the calibration process as to the analyzer 2x having not yet completed with the calibration. That is, as described above, it is determined at a predetermined time intervals whether or not the output value of each of the analyzers 2x is stable (Step S3), and in the case where the output value is stable, the output value and the known component concentration are compared using the output value thereafter to thereby perform the calibration of the analyzer 2x (Step S4). Thus, the respective completion times of the calibrations of the plurality of analyzers 2x are determined independently determined each other. When the calibration processes of the whole analyzers 2x are respectively completed (Step S6), the calibration processes of the plurality of analyzers 2x are finished.

According to the exhaust gas analyzing system 1 according to the present embodiment configured as described above, the plurality of analyzers 2x can be concurrently calibrated by concurrently supplying the calibration gas to the plurality of analyzers 2x via the calibration gas line 4. In addition, since the control unit 5 individually determines whether or not an output value of each of the plurality of analyzers 2x is stable and calibrates the analyzer 2x having the stable output value and then stops the supply of the calibration gas to the analyzer 2x upon completion of the calibration thereof, the calibration time can be optimized every individual analyzer 2x so that the calibration time can be reduced. Furthermore, since the calibration gas is not rendered to flow through the analyzer 2x having the stable output value in waste, the consumption amount of the calibration can be reduced.

It is noted that the present invention should not be limited to the above embodiment.

For example, in the present embodiment, although in any of the zero calibration and the span calibration the plurality of analyzers are individually calibrated and the supply of the calibration gas to the analyzers is stopped in sequence from the analyzer having completed with the calibration, any one of the zero calibration or the span calibration may be applied. In addition, as the span calibration, multi-point calibration may be performed using calibration gas of different concentrations.

In the embodiment, although the start of supplying the calibration gas are made at the same time to all of the plurality of analyzers to be supplied with the same calibration gas, the starting times of supplying the calibration gas to all of the plurality of analyzers to be supplied with the same may be different and there may be a time period in which the calibration gas is concurrently supplied to all of the plurality of analyzers during the calibration process. Furthermore, the start of supplying the calibration gas to at least two or more of the plurality of analyzers to be supplied with the same calibration gas is made at the same time and there may be a time period in which the calibration gas is concurrently supplied to all of the plurality of analyzers during the calibration process.

In addition, the calibration gas line may be adapted to concurrently supply the calibration gas to all of the plurality of analyzers to be supplied with the same calibration gas, and also may be adapted to concurrently supply the calibration gas to a part (at least two) of the plurality of analyzers.

Furthermore, the calibration of one analyzer may be also performed using the analyzer calibrating system of the present embodiment.

In addition, the present invention should not be limited to the above embodiment, and various modifications are of course possible within the scope unless departing from the intended spirit thereof.

DESCRIPTION OF REFERENCE NUMERALS

1 . . . Exhaust gas analyzing system
2 . . . Exhaust gas analyzing apparatus
2x . . . Analyzer
3 . . . Analyzer calibrating system
4 . . . Calibration gas line
4a . . . Zero gas line
4b . . . Span gas line
41 . . . Branch line
42 . . . On/off valve
5 . . . Control unit
6 . . . Calibration gas cylinder

What is claimed is:

1. An analyzer calibrating system for calibrating a plurality of exhaust gas analyzing apparatuses, the system comprising:
    a calibration gas line for concurrently supplying a same calibration gas, from a calibration gas cylinder arranged in a cylinder chamber partitioned from a plurality of test chambers, to a plurality of analyzers provided in each of the plurality of apparatuses, the plurality of apparatuses being provided in the plurality of test chambers respectively; and
    a control unit adapted to determine whether or not an output value of each of the plurality of analyzers supplied with the same calibration gas is stable,
    wherein the control unit is configured to calibrate each of the analyzers having the output value determined to be stable and to stop the supply of the calibration gas to each of the analyzers having completed the calibration,
    wherein the calibration gas line comprises a plurality of branch lines respectively provided in a one to one correspondence with the plurality of analyzers and a plurality of on/off valves respectively provided on the plurality of branch lines, and
    wherein the control unit is configured to control the on/off valve provided on each of the branch lines to stop the supply of the calibration gas to each of the analyzers having completed the calibration.

2. The analyzer calibrating system according to claim 1, wherein the calibration gas line comprises a zero gas line for supplying zero gas for zero calibration to the plurality of analyzers and a span gas line for supplying span gas for span calibration to the plurality of analyzers, and wherein the control unit is configured to carry out the zero calibration using the zero gas and the span calibration using the span gas in this order.

3. An exhaust gas analyzing system comprising the analyzer calibrating system according to claim 1.

* * * * *